(12) United States Patent
Zhao et al.

(10) Patent No.: US 7,871,953 B2
(45) Date of Patent: Jan. 18, 2011

(54) LATE TRANSITION METAL CATALYSTS FOR OLEFIN OLIGOMERIZATIONS

(75) Inventors: Baiyi Zhao, Kingwood, TX (US); Smita Kacker, Houston, TX (US); Jo Ann Marie Canich, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 231 days.

(21) Appl. No.: 10/692,827

(22) Filed: Oct. 24, 2003

(65) Prior Publication Data

US 2005/0003955 A1    Jan. 6, 2005

Related U.S. Application Data

(60) Provisional application No. 60/421,359, filed on Oct. 25, 2002, provisional application No. 60/421,486, filed on Oct. 25, 2002.

(51) Int. Cl.
    B01J 31/00    (2006.01)
    B01J 21/02    (2006.01)
    B01J 27/00    (2006.01)
    B01J 27/185   (2006.01)

(52) U.S. Cl. .................. 502/150; 502/162; 502/167; 502/169; 502/207; 502/208; 502/213

(58) Field of Classification Search ................ 502/150, 502/162, 167, 169, 207, 208, 213
See application file for complete search history.

(56) References Cited

U.S. PATENT DOCUMENTS

| | | | |
|---|---|---|---|
| 3,991,259 A * | 11/1976 | Piekarski et al. ............... 526/97 |
| 4,824,977 A | 4/1989 | Devon et al. | |
| 4,904,808 A | 2/1990 | Devon et al. | |
| 5,658,982 A * | 8/1997 | Baardman et al. ........... 524/711 |
| 5,777,087 A | 7/1998 | Kohlpaintner et al. | |
| 5,994,255 A | 11/1999 | Nickias et al. | |
| 6,184,381 B1 | 2/2001 | Ikariya et al. | |
| 6,225,487 B1 * | 5/2001 | Guram ......................... 556/18 |
| 6,262,196 B1 * | 7/2001 | Mecking ..................... 526/114 |
| 6,307,087 B1 * | 10/2001 | Buchwald et al. ........... 558/388 |
| 6,323,353 B1 * | 11/2001 | Sumi et al. .................... 556/21 |
| 6,525,210 B1 | 2/2003 | Zhang et al. | |
| 6,632,901 B2 | 10/2003 | McCullough | |
| 6,710,007 B2 * | 3/2004 | Brookhart et al. ........... 502/155 |
| 7,247,687 B2 | 7/2007 | Cherkasov et al. | |
| 2002/0107342 A1 * | 8/2002 | Mawson et al. ............. 526/129 |
| 2002/0197731 A1 * | 12/2002 | McFarland et al. .......... 436/171 |
| 2003/0032808 A1 * | 2/2003 | Peters et al. .................... 546/2 |
| 2005/0003955 A1 | 1/2005 | Zhao et al. .................. 502/150 |

FOREIGN PATENT DOCUMENTS

| | | |
|---|---|---|
| EP | 0 479 541 A1 | 4/1992 |
| JP | 09255713 | 9/1997 |
| WO | WO 00/02887 A2 | 1/2000 |
| WO | WO 01/38337 A2 | 5/2001 |
| WO | WO 2004/037837 | 5/2004 |
| WO | WO 2004/037869 | 5/2004 |

OTHER PUBLICATIONS

JP-09-255713, Sep. 30, 1997, Chem. Abstracts #127:359235, Tomohiro Yorisue.*
McDonough, James Eric; Thermodynamics and Kinetic studies of ligand binding, oxidative addition, and Group/Atom transfer in Group VI Metal Complexes; Dec. 2005, University of Miami; p. 66.*
http://en.wikipedia.org/wiki/Ligand_field_theory.*
http://en.wikipedia.org/wiki/Ligand.*
Kocovsky et al. J. Am. Chem. Soc. 1999, 121, 7714-7715.*
Qian et al. "Synthesis and Polymerization Behavior of Various Substituted Half-Sandwich Titanium Complexes CP'TiCl2(OR*) as Catalyst for Syndiotactic polystyrene"; J. Mol. Cat.; 208; 2004, 45-54.*
Fabian et al.; "Modeling the Chromatic Enantioseparation of Aryl- and Hetarycarbinols on ULMO, a Brush-Type Chiral Stationary phase, by 3D-QSAR Techniques"; Chirality 15:271-275 (2003).*
Daniel C.; "Quantitative Chemical Analysis"; fifth edition; 1982; pp. 306-329.*
Shiver et al.; "Inorganic Chemistry" third edition; 1999 pp. 245-247, 467-482, and 562.*
Dieter Vogt, "Olgomerization of Ethylene to Higher Linear α-Olefins", Ed. Applied Homogeneous Catalysis with Organoinetallic Compounds, A Comprehensive Handbook, vol. 1, VCH Verlagsgesellschaft mbH, Weinheim, 1996, pp. 245-258.
B. Elvers, et al. "Hydrocarbons", Ed. Ullmann's Encyclopedia of Industrial Chemistry, vol. A13, VCH Verlagsgesellschaft mbH, Weinheim, 1989, pp. 243-247 and 275-276.

(Continued)

Primary Examiner—Jerry Lorengo
Assistant Examiner—James E McDonough
(74) Attorney, Agent, or Firm—Catherine L. Bell

(57) ABSTRACT

As series of novel late transition metal catalysts for olefin oligomerization have been invented. The catalyst system includes a Group 8, 9 or 10 transition metal and an activator. The catalysts demonstrate high activity and selectivity for linear α-olefins. Preferably this invention relates to a catalyst system comprising the reaction product of: (a) an activator selected from the group consisting of alumoxane, aluminum alkyl, alkyl aluminum halide, alkylaluminum alkoxide, discrete ionic activator, and Lewis acid; and (b) a catalyst precursor wherein the catalyst precursor has the following formula:

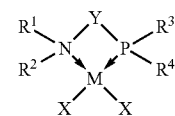

wherein (i) M is a Group-8, -9 , or -10 transition metal; (ii) N is nitrogen (iii) P is phosphorus; (iv) $R^1$, $R^2$, $R^3$, and $R^4$ are independently hydrocarbyl radicals; (v) Y is a hydrocarbyl bridge comprising a backbone wherein the backbone comprises a chain that is four or more carbon atoms long; (vi) X are independently abstractable ligands.

25 Claims, No Drawings

OTHER PUBLICATIONS

Gandelman, Mark et al, "*The First Observation and Kinetic Evaluation of a Single Step Metal Insertion into a C-C Bond*", Journal of the American Chemical Society (2000), 122(40), pp. 9848-9849, XP002241620.

Kamigaito, Masami et at "*Transition metal-catalyzed living radical polymerization: latest advances*", American Chemical Society, Division of Polymer Chemistry, (2002), 43(2), 3-4, 2002 (Abstract).

David W. Old et al., "*A Highly Active Catalyst for Palladium-Catalyzed Cross-Coupling Reactions: Room-Temperature Suzuki Couplings and Amination of Unactivated Aryl Chlorides*", J. Am. Chem. Soc., 1998, 120, pp. 9722-9723.

John P. Wolfe et al., "*Highly Active Palladium Catalysts for Suzuki Coupling Reactions*", J. Am. Chem. Soc. 1999, 121, pp. 9550-9561.

Joseph M. Fox et al., "*Highly Active and Selective Catalysts for the Formation of α-Aryl Ketones*", J. Am. Chem. Soc. 2000, 122, pp. 1360-1370.

Pavel Kocovsky et al., "*Palladium(II) Complexes of 2-Dimethylamino-2 'diphenylphosphino: 1,1 '-binaphthyl (MAP) with Unique Pc,Co Coordination and Their Catalytic Activity in Allylic Substitution, Hartwig-Buchwald Amination, and Suzuki Coupling*", J. Am. Chem. Soc. 1999, 121, pp. 7714-7715.

U.S. Appl. No. 10/693,584, filed Oct. 24, 2003, Zhao et al.

Yorisue, Tomohiro, "Polymerization catalysts for manufacture of branched polyolefins with high molecular weight and narrow molecular weight distribution", XP002241622, Asahi Chemical Industry Co., Ltd., Japan, 1997, Database accession No. 127:359-235 CA abstract & JP 09 255713 A.

Kaminsky et al., "Fluorinated Half-Sandwich Complexes as Catalysts in Syndiospecific Styrene Polymerization", Macromolecules, 1997, 30, pp. 7647-7650.

Kocovsky et al., "Palladium(II) Complexes of 2-Dimethylamino-2'-diphenylphosphino-1,1'-binaphthyl (MAP) with Unique P,C$_o$-Coordination and Their Catalytic Activity in Allylic Substitution, Hartwig-Buchwald Amination, and Suzuki Coupling", J. Am. Chem. Soc., 1999, 121, pp. 7714-7715.

Fox et al., "Highly Active and Selective Catalysts for the Formation of α-Aryl Ketones", J. Am. Chem. Soc., 2000, 122, pp. 1360-1370.

Milani et al., "Highly Efficient Catalytic System for the CO/Styrene Copolymerization: Toward the Stabilization of the Active Species", Organometallics 2000, 19, pp. 3435-3441.

Nozaki, "Tacticity in Ethylene/Carbon Monoxide/Vinyl Co- and Terpolymerizations, Stereoselective Polymerization with Single-Site Catalysts", CRC Press, 2008, pp. 577-591.

Pedeutour et al., "Influence of X ligand nature in the activation process of *rac*Et(Ind)$_2$ZrX$_2$ by methylaluminoxane", J. Mol. Catalysis A:Chemical, 2001, 176, pp. 87-94.

Christmann et al., Experimental and Theoretical Investigations of New Dinuclear Palladium Complexes as Precatalysts for the Amination of Aryl Chlorides, J. Am. Chem. Soc., 2006, vol. 128, No. 19, pp. 6376-6390.

Derwent Abstract, CAS Registry No. 213697-53-1, [1,1'-Biphenyl]-2-amine, 2'(dicyclohexylphosphino)-N,N-dimethyl- (9C1), Jul. 13, 2001.

\* cited by examiner

LATE TRANSITION METAL CATALYSTS FOR OLEFIN OLIGOMERIZATIONS

CLAIM FOR PRIORITY

This application claims priority from U.S. Ser. No. 60/421,359 filed Oct. 25, 2002 and U.S. Ser. No. 60/421,486 filed Oct. 25, 2002.

TECHNICAL FIELD

This document relates to late transition metal catalysts for olefin oligomerizations and to methods for making and using these catalysts.

BACKGROUND OF THE INVENTION

Alpha-olefins, especially those containing 6 to 20 carbon atoms, are important items of commerce. They are used as intermediates in the manufacture of detergents, as monomers (especially in linear low-density polyethylene), and as intermediates for many other types of products. Consequently, improved methods of making these compounds are desired. Especially desired, is a process capable of making a range of linear α-olefins such as 1-butene and 1-hexene.

Most commercially produced α-olefins are made by the oligomerization of ethylene, catalyzed by various types of compounds, see for instance B. Elvers, et al., Ed. Ullmann's Encyclopedia of Industrial Chemistry, Vol. A13, VCH Verlagsgesellschaft mbH, Weinheim, 1989, p. 243-247 and 275-276, and B. Cornils, et al., Ed., Applied Homogeneous Catalysis with Organometallic Compounds, A Comprehensive Handbook, Vol. 1, VCH Verlagsgesellschaft mbH, Weinheim, 1996, p. 245-258. The major types of commercially used catalysts are alkylaluminum compounds, certain nickel-phosphine complexes, and a titanium halide with a Lewis acid such as $AlCl_3$. In all of these processes, significant amounts of branched internal olefins and diolefins are produced. Since in most instances these are undesirable and often difficult to separate, these byproducts are avoided commercially.

SUMMARY

Invention catalyst systems, suitable for solution- or slurry-phase oligomerization reactions to produce α-olefins, comprise a Group-8, -9, or -10 transition metal component (catalyst precursor) and an activator. Invention catalyst precursors can be represented by the general formula:

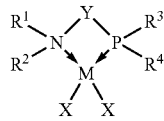

where M is a Group-8, -9, or -10 transition metal, especially Fe, Co and Ni; N is nitrogen; P is phosphorous; Y is a hydrocarbyl bridge in which four or more carbon atoms connect between the nitrogen and phosphorus atoms; $R^1$, $R^2$, $R^3$ and $R^4$ are independently hydrocarbyl radicals such as $C_1$-$C_{40}$ aliphatic radicals, $C_3$-$C_{40}$ alicyclic radicals, $C_6$-$C_{40}$ aromatic radicals or combinations of these; X is independently a hydride radical, a hydrocarbyl radical, or hydrocarbyl-substituted organometalloid radical; or two X's are connected and form a 3 to 50 atom metallacycle ring. When Lewis-acid activators such as methylalumoxane, aluminum alkyls, alkylaluminum alkoxides or alkylaluminum halides that are capable of donating an X ligand, as described above, to the transition metal component are used, or when the ionic activator is capable of extracting X, one or more X, which may optionally be bridged to one another, may additionally be independently selected from a halogen, alkoxide, aryloxide, amide, phosphide or other anionic ligand, provided that the resulting activated catalyst contains as least one M-H or M-C bond into which an olefin can insert.

DEFINITIONS

The term "Y" as used herein refers to a hydrocarbyl bridge, as further defined herein.

The term "hydrocarbyl radical" is sometimes used interchangeably with "hydrocarbyl" throughout this document. For purposes of this disclosure, "hydrocarbyl radical" encompasses $C_1$-$C_{50}$ radicals. These radicals can be linear, branched, or cyclic, and when cyclic, aromatic or non-aromatic. Thus, the term "hydrocarbyl radical", in addition to unsubstituted hydrocarbyl radicals, encompasses substituted hydrocarbyl radicals, halocarbyl radicals, and substituted halocarbyl radicals, as these terms are defined below.

Substituted hydrocarbyl radicals are radicals in which at least one hydrogen atom has been substituted with at least one functional group such as $NR''_2$, $OR''$, $PR''_2$, $SR''$, $BR''_2$, $SiR''_3$, $GeR''_3$ and the like or where at least one non-hydrocarbon atom or group has been inserted within the hydrocarbyl radical, such as O, S, NR'', PR'', BR'', $SiR''_2$, $GeR''_2$, and the like, where R'' is independently a hydrocarbyl or halocarbyl radical. The functional group can be an organometalloid radical.

Halocarbyl radicals are radicals in which one or more hydrocarbyl hydrogen atoms have been substituted with at least one halogen or halogen-containing group (e.g. F, Cl, Br, I).

Substituted halocarbyl radicals are radicals in which at least one hydrocarbyl hydrogen or halogen atom has been substituted with at least one functional group such as $NR''_2$, $OR''$, $PR''_2$, $SR''$, $BR''_2$, $SiR''_3$, $GeR''_3$ and the like or where at least one non-carbon atom or group has been inserted within the halocarbyl radical such as O, S, NR'', PR'', BR'', $SiR''_2$, $GeR''_2$, and the like where R'' is independently a hydrocarbyl or halocarbyl radical provided that at least one halogen atom remains on the original halocarbyl radical. The functional group can be an organometalloid radical.

In some embodiments, the hydrocarbyl radical is independently selected from methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, or triacontynyl isomers. For this disclosure, when a radical is listed it indicates that radical type and all other radicals formed when that radical type is subjected to the substitutions defined above. Alkyl, alkenyl and alkynyl radicals listed include all isomers including where appropriate cyclic isomers, for example, butyl includes n-butyl, 2-methylpropyl, 1-methylpropyl, tert-butyl, and cyclobutyl (and analogous substituted cyclopropyls); pentyl includes n-pentyl, cyclopentyl, 1-methylpentyl, 2-methylbutyl, 3-methylbutyl, 1-ethylpropyl, and neopentyl (and analogous substituted cyclobutyls and cyclopropyls); butenyl includes E and Z forms of 1-butenyl, 2-butenyl, 3-butenyl, 1-methyl-1-propenyl, 1-methyl-2-propenyl, 2-methyl-1-propenyl and 2-methyl-2-propenyl (and cyclobutenyls and cyclopropenyls).

The transition metal component can also be described as comprising at least one ancillary ligand that stabilizes the oxidation state of the metal. Ancillary ligands serve to enforce the geometry around the metal center. In this disclosure, ancillary ligands have a backbone that comprises nitrogen and phosphorous bridged to each other by at least 4 atoms.

For purposes of this disclosure, oligomers include about 2-75 mer units. A mer is defined as a unit of an oligomer or polymer that originally corresponded to the olefin that was used in the polymerization reaction. For example, the mer of polyethylene would be ethylene.

Abstractable ligands are ligands that are removed from the catalyst precursor to activate it. They are sometimes assigned the label X in this disclosure. X are independently hydride radicals, hydrocarbyl radicals, or hydrocarbyl-substituted organometalloid radicals; or two X's are connected and form a 3-to-50-atom metallacycle ring. When Lewis-acid activators such as methylalumoxane, aluminum alkyls, alkylaluminum alkoxides or alkylaluminum halides that are capable of donating an X ligand, as described above, to the transition metal component are used, or when the ionic activator is capable of extracting X, one or more X, which may optionally be bridged to one another, may additionally be independently selected from a halogen, alkoxide, aryloxide, amide, phosphide or other anionic ligand, provided that the resulting activated catalyst contains as least one M-H or M-C connection in which an olefin can insert.

In some structures throughout this specification the ligand-metal connection is drawn with an arrow indicating that the electrons originally came from the ligand. At other times, the connection is shown by drawing a solid line. One of ordinary skill in the art recognizes that these depictions are interchangeable.

$C_6F_5$ is pentafluorophenyl or perfluorophenyl. $C_6H_5$ is phenyl.

For purposes of this document the term "comprising" is interchangeable with "including".

DETAILED DESCRIPTION

In one embodiment of this invention, the catalyst precursor can be represented by the following formula:

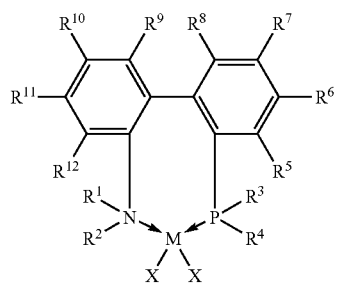

where M, N, P, $R^1$, $R^2$, $R^3$, $R^4$ and X are defined above, and $R^5$, $R^6$, $R^7$, $R^8$, $R^9$, $R^{10}$, $R^{11}$, and $R^{12}$ are independently hydrogen, fluorine, or $C_1$-$C_{20}$ hydrocarbyl radicals. The organic group connecting between N and P takes the place of Y, the hydrocarbyl bridge.

In other invention embodiments, $R^1$ and $R^2$ are independently $C_1$-$C_{12}$ hydrocarbyl radicals, $C_1$-$C_6$ hydrocarbyl radicals, or methyl radicals. In these or other embodiments, $R^3$ and $R^4$ are independently $C_6$-$C_{20}$ hydrocarbyl radicals, $C_6$-$C_{12}$ hydrocarbyl radicals, aromatic radicals, cyclohexyl radicals, or phenyl radicals.

Specific, invention catalyst precursor examples are illustrated by the following formula where some components are listed in Table 1. For Y, alkylenes are diradicals and include all isomers of bridge length 4 or greater, for example, hexylene includes 1,6-hexylene, 2,5-hexylene, 2-methyl-1,5-pentylene, 3-methyl-1,5-pentylene, 4-methyl-1,5-pentylene, 1,5-hexylene, 3,6-hexylene, 2-ethyl-1,4-butylene, 3-ethyl-1,4-butylene, 4-ethyl-1,4-butylene, and 1,4-hexylene. To illustrate members of the transition metal component, select any combination listed in Table 1. For example, by choosing the first row components, the transition metal compound would be 1-(N,N-dimethylamino)-4-(P,P-dimethylphosphino)butylene nickel dichloride. By selecting a combination of components from Table 1, an example would be 2-(N,N-dimethlamino)-2'-(P,P-dicyclohexylphosphino)biphenyl nickel dibromide. Any combination of components may be selected.

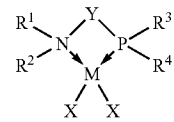

| $R^1$, $R^2$, $R^3$, and $R^4$ | Y | $X^1$ and $X^2$ | M |
|---|---|---|---|
| methyl | Butylene | chloride | nickel |
| ethyl | Pentylene | bromide | iron |
| propyl | Hexylene | iodide | cobalt |
| butyl | Heptylene | methyl | palladium |
| pentyl | Octylene | ethyl | platinum |
| hexyl | Nonylene | propyl | ruthenium |
| heptyl | Decylene | butyl | osmium |
| octyl | Undecylene | pentyl | rhodium |
| nonyl | Dodecylene | hexyl | iridium |
| decyl | Tridecylene | heptyl | |
| Undecyl | Tetradecylene | octyl | |
| Dodecyl | Pentadecylene | nonyl | |
| Tridecyl | Hexadecylene | decyl | |
| Tetradecyl | Heptadecylene | undecyl | |
| Pentadecyl | Octadecylene | dodecyl | |
| Hexadecyl | Nonadecylene | tridecyl | |
| Heptadecyl | Eicosylene | tetradecyl | |
| Octadecyl | Heneicosylene | pentadecyl | |
| Nonadecyl | Docosylene | hexadecyl | |
| eicosyl | tricosylene | heptadecyl | |
| Heneicosyl | tetracosylene | octadecyl | |
| Docosyl | pentacosylene | nonadecyl | |
| Tricosyl | hexacosylene | eicosyl | |
| Tetracosyl | heptacosylene | heneicosyl | |
| Pentacosyl | octacosylene | docosyl | |
| Hexacosyl | nonacosylene | tricosyl | |
| Heptacosyl | triacontylene | tetracosyl | |
| Octacosyl | cyclohexylene | pentacosyl | |
| Nonacosyl | cyclooctylene | hexacosyl | |
| Triacontyl | cyclodecylene | heptacosyl | |
| Ethenyl | cyclododecylene | octacosyl | |
| Propenyl | 2,2'-biphenyl | nonacosyl | |
| Butenyl | butenylene | triacontyl | |
| Pentenyl | penentylene | hydride | |

-continued

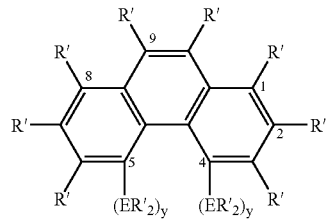

| $R^1$, $R^2$, $R^3$, and $R^4$ | Y | $X^1$ and $X^2$ | M |
|---|---|---|---|
| Hexenyl | hexenylene | phenyl | |
| Heptenyl | heptenylene | benzyl | |
| Octenyl | octenylene | phenethyl | |
| Nonenyl | nonenylene | tolyl | |
| Decenyl | decenylene | methoxy | |
| Undecenyl | undecenylene | ethoxy | |
| Dodecenyl | dodecenylene | propoxy | |
| Ethynyl | hexynylene | butoxy | |
| Propynyl | heptynylene | dimethylamino | |
| Butynyl | octynylene | diethylamino | |
| Pentynyl | nonynylene | methylethylamino | |
| Hexynyl | decynylene | phenoxy | |
| Heptynyl | undecynylene | benzoxy | |
| Octynyl | dodecynylene | allyl | |
| Nonynyl | butadienylene | 1,1-dimethyl allyl | |
| Decynyl | pentadienylene | 2-carboxymethyl allyl | |
| Undecynyl | hexadienylene | acetylacetonate | |
| Dodecynyl | heptadienylene | 1,1,1,5,5,5-hexa-fluoroacetylacetonate | |
| phenyl | octadienylene | 1,1,1-trifluoro-acetylacetonate | |
| benzyl | nonadienylene | 1,1,1-trifluoro-5,5-di-methylacetylacetonate | |
| Phenethyl | decadienylene | | |
| tolyl | undecadienylene | both $X^1$ and $X^2$ | |
| Cyclobutyl | dodecadienylene | catecholate | |
| Cyclopentyl | hexatrienylene | 3,5-dibutylcatecholate | |
| Cyclohexyl | octatrienylene | 3,6-dibutylcatecholate | |
| Cycloheptyl | decatrienylene | 3,6-dibutyl-4,5-di-methoxycatecholate | |
| Cyclooctyl | dodecatrienylene | 3,6-dibutyl-4,5-di-chlorocatecholate | |
| Cyclononyl | | 3,6-dibutyl-4,5-di-bromocatecholate | |
| Cyclodecyl | | 1,3-propylene | |
| Cyclododecyl | | 1,4-butylene | |

$R^3$ and $R^4$ can further independently be defined as one of the following substituents:

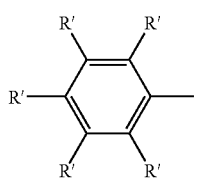 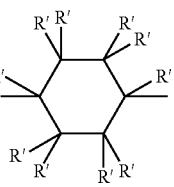

where R' are independently, hydrogen or $C_1$-$C_{50}$ hydrocarbyl radicals. Additionally, any two adjacent R' may independently be joined to form a saturated or unsaturated cyclic structure.

Y can further be defined as one of the following bridging groups:

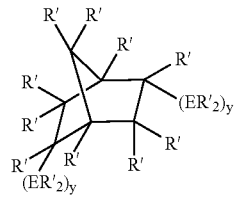

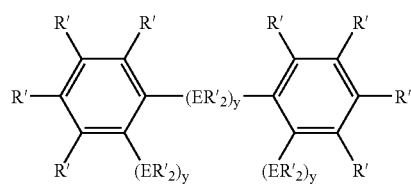

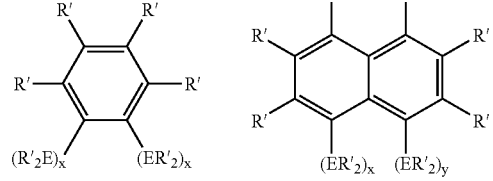

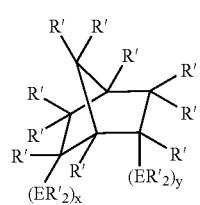 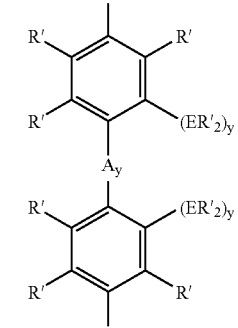

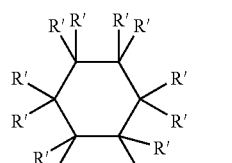 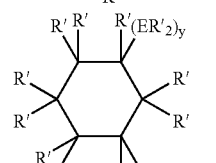

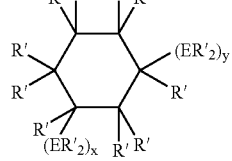 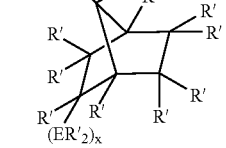

-continued

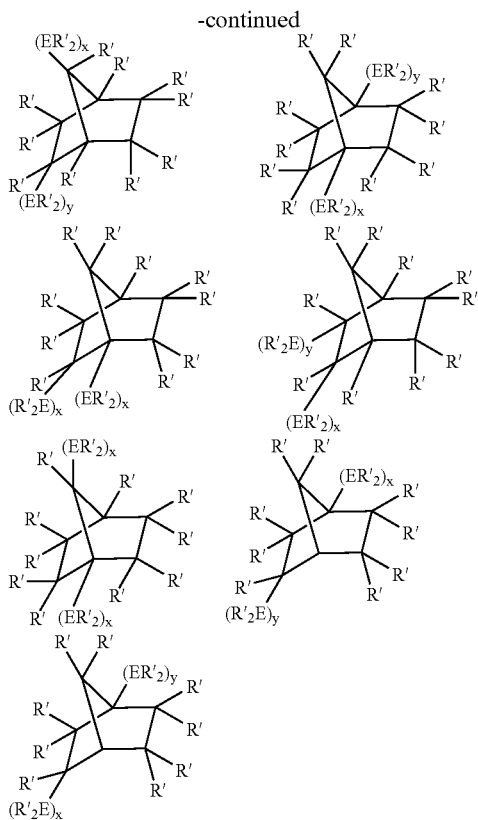

where R' is as defined above, A is a non-hydrocarbon atom or group (i.e. C=O, C=S, O, S, SO$_2$, NR*, PR*, BR*, SiR*$_2$, GeR*$_2$ and the like where R* is independently a hydrocarbyl or halocarbyl radical), E is a Group-14 element including carbon, silicon and germanium, x is an integer from 1 to 4, and y is an integer from 0 to 4.

Common activators are useful with this invention: alumoxanes, such as methylalumoxane, modified methylalumoxane, ethylalumoxane and the like; aluminum alkyls such as trimethyl aluminum, triethyl aluminum, triisopropyl aluminum and the like; alkyl aluminum halides such as diethyl aluminum chloride and the like; and alkylaluminum alkoxides.

The alumoxane component useful as an activator typically is an oligomeric aluminum compound represented by the general formula (R'''—Al—O)$_n$, which is a cyclic compound, or R''(R''—Al—O)$_n$AlR''$_2$, which is a linear compound. In the general alumoxane formula, R'' is independently a C$_1$-C$_{20}$ alkyl radical, for example, methyl, ethyl, propyl, butyl, pentyl, isomers thereof, and the like, and "n" is an integer from 1-50. Most preferably, R'' is methyl and "n" is at least 4. Methylalumoxane and modified methylalumoxanes are most preferred. For further descriptions see, EP 279586, EP 561476, WO94/10180 and U.S. Pat. Nos. 4,665,208, 4,908, 463, 4,924,018, 4,952,540, 4,968,827, 5,041,584, 5,103,031, 5,157,137, 5,235,081, 5,248,801, 5,329,032, 5,391,793, and 5,416,229.

The aluminum alkyl component useful as an activator is represented by the general formula R''AlZ$_2$ where R'' is defined above, and each Z is independently R'' or a different univalent anionic ligand such as halogen (Cl, Br, I), alkoxide (OR'') and the like. Most preferred aluminum alkyls include triethylaluminum, diethylaluminum chloride, triisobutylaluminum, tri-n-octylaluminum and the like.

When alumoxane or aluminum alkyl activators are used, the catalyst-precursor-to-activator molar ratio is from about 1:1000 to 10:1; alternatively, 1:500 to 1:1; or 1:300 to 1:10.

Additionally, discrete ionic activators such as [Me$_2$PhNH] [B(C$_6$F$_5$)$_4$], [BU$_3$NH][BF$_4$], [NH$_4$][PF$_6$], [NH$_4$][SbF$_6$], [NH$_4$][AsF$_6$], [NH$_4$][B(C$_6$H$_5$)$_4$] or Lewis acidic activators such as B(C$_6$F$_5$)$_3$ or B(C$_6$H$_5$)$_3$ can be used, if they are used in conjunction with a compound capable of alkylating the metal such as an alumoxane or aluminum alkyl. Discrete ionic activators provide for an activated catalyst site and a relatively non-coordinating (or weakly coordinating) anion. Activators of this type are well known in the literature, see for instance W. Beck., et al., Chem. Rev., Vol. 88, p. 1405-1421 (1988); S. H. Strauss, Chem. Rev., Vol. 93, p. 927-942 (1993); U.S. Pat. Nos. 5,198,401, 5,278,119, 5,387,568, 5,763,549, 5,807,939, 6,262,202, and WO93/14132, WO99/45042 WO01/30785 and WO01/42249.

Invention catalyst precursors can also be activated with cocatalysts or activators that comprise non-coordinating anions containing metalloid-free cyclopentadienide ions. These are described in U.S. Patent Publication 2002-0058765 A1, published on 16 May 2002.

When a discrete ionic activator is used, the catalyst-precursor-to-activator molar ratio is from 1:10 to 1.2:1; 1:10 to 10:1; 1:10 to 2:1; 1:10 to 3:1; 1:10 to 5:1; 1:2 to 1.2:1; 1:2 to 10:1; 1:2 to 2:1; 1:2 to 3:1; 1:2 to 5:1; 1:3 to 1.2:1; 1:3 to 10:1; 1:3 to 2:1; 1:3 to 3:1; 1:3 to 5:1; 1:5 to 1.2:1; 1:5 to 10:1; 1:5 to 2:1; 1:5 to 3:1; 1:5 to 5:1.

The catalyst-precursor-to-alkylating-agent molar ratio is from 1:10 to 10:1; 1:10 to 2:1; 1:10 to 25:1; 1:10 to 3:1; 1:10 to 5:1; 1:2 to 10:1; 1:2 to 2:1; 1:2 to 25:1; 1:2 to 3:1; 1:2 to 5:1; 1:25 to 10:1; 1:25 to 2:1; 1:25 to 25:1; 1:25 to 3:1; 1:25 to 5:1; 1:3 to 10:1; 1:3 to 2:1; 1:3 to 25:1; 1:3 to 3:1; 1:3 to 5:1; 1:5 to 10:1; 1:5 to 2:1; 1:5 to 25:1; 1:5 to 3:1; 1:5 to 5:1.

The catalyst systems of this invention can additionally be prepared by combining in any order, the bidentate ligand:

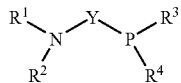

where N, P, Y, R$^1$, R$^2$, R$^3$ and R$^4$ are as previously defined and a Group-8, -9, or -10 halide salt which may optionally be coordinated by solvent (for example NiX$_2$ or NiX$_2$.MeOCH$_2$CH$_2$OMe where X=Cl, Br or I) in an activator-compound solution (for example methylalumoxane dissolved in toluene). The reactants may be added in any order, or even essentially simultaneously.

Invention catalyst precursor solubility allows for the ready preparation of supported catalysts. To prepare uniform supported catalysts, the catalyst precursor should significantly dissolve in the chosen solvent. The term "uniform supported catalyst" means that the catalyst precursor or the activated catalyst approach uniform distribution upon the support's accessible surface area, including the interior pore surfaces of porous supports.

Invention supported catalyst systems may be prepared by any method effective to support other coordination catalyst systems, effective meaning that the catalyst so prepared can be used for oligomerizing olefin in a heterogeneous process. The catalyst precursor, activator, suitable solvent, and support may be added in any order or simultaneously. In one invention embodiment, the activator, dissolved in an appropriate solvent such as toluene is stirred with the support material for 1 minute to 10 hours. The total volume of the activation solution may be greater than the pore volume of the support, but some embodiments limit the total solution volume below that needed to form a gel or slurry (about 100-200% of the pore volume). The mixture is optionally heated to 30-200° C. during this time. The catalyst can be added to this mixture as a solid, if a suitable solvent is employed in the previous step, or as a solution. Or alternatively, this mixture can be filtered, and the resulting solid mixed with a catalyst precursor solution. Similarly, the mixture may be vacuum dried and mixed with a catalyst precursor solution. The resulting catalyst mixture is then stirred for 1 minute to 10 hours, and the catalyst is either filtered from the solution and vacuum dried, or vacuum or evaporation alone removes the solvent.

In another invention embodiment, the catalyst precursor and activator are combined in solvent to form a solution. The support is then added to this solution and the mixture is stirred for 1 minute to 10 hours. The total volume of this solution may be greater than the pore volume of the support, but some embodiments limit the total solution volume below that needed to form a gel or slurry (about 100-200% pore volume). The residual solvent is then removed under vacuum, typically at ambient temperature and over 10-16 hours. But greater or lesser times are possible.

The catalyst precursor may also be supported in the absence of the activator, in which case the activator is added to the liquid phase of a slurry process. For example, a solution of catalyst precursor is mixed with a support material for a period of about 1 minute to 10 hours. The resulting catalyst precursor mixture is then filtered from the solution and dried under vacuum, or vacuum or evaporation alone removes the solvent. The total volume of the catalyst precursor solution may be greater than the pore volume of the support, but some embodiments limit the total solution volume below that needed to form a gel or slurry (about 100-200% of the pore volume).

Additionally, two or more different catalyst precursors may be placed on the same support using any of the support methods disclosed above. Likewise, two or more activators may be placed on the same support.

Suitable solid particle supports typically comprise polymeric or refractory oxide materials. Some embodiments select porous supports (such as for example, talc, inorganic oxides, inorganic chlorides (magnesium chloride)) that have an average particle size greater than 10 μm. Some embodiments select inorganic oxide materials as the support material including Group-2, -3, -4, -5, -13, or -14 metal or metalloid oxides. Some embodiments select the catalyst support materials to include silica, alumina, silica-alumina, and their mixtures. Other inorganic oxides may serve either alone or in combination with the silica, alumina, or silica-alumina. These are magnesia, titania, zirconia, and the like. Lewis acidic materials such as montmorillonite and similar clays may also serve as a support. In this case, the support can optionally double as the activator component. But additional activator may also be used.

As well know in the art, the support material may be pretreated by any number of methods. For example, inorganic oxides may be calcined, and/or chemically treated with dehydroxylating agents such as aluminum alkyls and the like.

Some embodiments select the carrier of invention catalysts to have a surface area of 10-700 $m^2/g$, or pore volume of 0.1-4.0 cc/g, and average particle size from 10-500 μm. But greater or lesser values may also be used.

Invention catalysts may generally be deposited on the support at a loading level of 10-100 micromoles of catalyst precursor per gram of solid support; alternately from 20-80 micromoles of catalyst precursor per gram of solid support; or from 40-60 micromoles of catalyst precursor per gram of support. But greater or lesser values may be used. Some embodiments select greater or lesser values, but require that the total amount of solid catalyst precursor does not exceed the support's pore volume.

Additionally, oxidizing agents may be added to the supported or unsupported catalyst as described in WO 01/68725.

Invention polymerization catalyst systems can comprise additional olefin polymerization catalysts. These additional olefin polymerization catalysts are any of those well known in the art to catalyze the olefin to polyolefin reaction. Some invention catalysts systems include Group-4-6 metallocenes as additional olefin polymerization catalysts. Metallocenes include (un)bridged compounds containing one (mono(cyclopentadienyl) metallocenes) or two (bis(cyclopentadienyl) metallocenes) (un)substituted cyclopentadienyl ligand(s). In bridged metallocenes, a single, cyclopentadienyl ligand connects to a heteroatom ligand with both coordinating to the metal center, or two cyclopentadienyl ligands connect together with both cyclopentadienyl ligands coordinating to the metal center. Typical catalysts and their precursors are well known in the art. Suitable description appears in the patent literature, for example U.S. Pat. Nos. 4,871,705, 4,937, 299, 5,324,800, EP-A-0418044, EP-A-0591756, WO-A-92/00333 and WO-A-94/01471. Some embodiments select the metallocene compounds from mono- or bis-cyclopentadienyl-substituted, Group-4, -5, and -6 metals in which cyclopentadienyls are (un)substituted with one or more groups or are bridged to each other or to a metal-coordinated heteroatom. Some embodiments select similar metallocene compounds except they are not necessarily bridged to each other or to a metal-coordinated heteroatom. See U.S. Pat. Nos. 5,278,264 and 5,304,614.

Some invention catalysts systems include the following additional olefin polymerization catalysts. Metallocene compounds suitable for linear polyethylene or ethylene-containing copolymer production (where copolymer means comprising at least two different monomers) are essentially those disclosed in WO-A-92/00333, WO 97/44370 and U.S. Pat. Nos. 5,001,205, 5,057,475, 5,198,401, 5,304,614, 5,308,816 and 5,324,800. Selection of metallocene compounds for isotactic or syndiotactic polypropylene blend production, and their syntheses, are well-known in the patent and academic literature, e.g. *Journal of Organometallic Chemistry* 369, 359-370 (1989). Typically, those catalysts are stereorigid, asymmetric, chiral, or bridged-chiral metallocenes. Invention activators are suited for activating these types of catalyst precursors.

Likewise, some invention catalysts systems include the following additional olefin polymerization catalysts: monocyclopentadienyl metallocenes with Group-15 or -16 heteroatoms connected, through a bridging group, to a cyclopentadienyl-ligand ring carbon. Both the cyclopentadienyl Cp-ligand and the heteroatom connect to a transition metal. Some embodiments select a Group-4 transition metal. Additionally, unbridged monocyclopentadienyl, heteroatom-containing Group-4 components of WO 97/22639 will function with this invention. Moreover, transition metal systems with high-oxidation-state, Group-5-10 transition-metal centers are known and can serve as the additional olefin polymerization catalysts with invention catalyst systems.

Invention catalyst systems can use non-cyclopentadienyl, Group-4-5 precursor compounds as the additional olefin polymerization catalysts. Non-cyclopentadienyl, Group-4-5 precursor compounds are activable to stable, discrete cationic complexes include those containing bulky, chelating, diamide ligands, such as described in U.S. Pat. No. 5,318,935 and "Conformationally Rigid Diamide Complexes: Synthesis and Structure of Tantalum (III) Alkyne Derivatives", D. H. McConville, et al, *Organometallics* 1995, 14, 3154-3156. U.S. Pat. No. 5,318,935 describes bridged and unbridged, bis-amido catalyst compounds of Group-4 metals capable of α-olefins polymerization. Bridged bis(arylamido) Group-4 compounds for olefin polymerization are described by D. H. McConville, et al., in *Organometallics* 1995, 14, 5478-5480.

Synthetic methods and compound characterization are presented. Further work appearing in D. H. McConville, et al, *Macromolecules* 1996, 29, 5241-5243, describes bridged bis (arylamido) Group-4 compounds that are polymerization catalysts for 1-hexene. Additional invention-suitable transition-metal compounds include those described in WO 96/40805. Cationic Group-3- or Lanthanide olefin polymerization complexes are disclosed in copending U.S. application Ser. No. 09/408,050, filed 29 Sep. 1999, and its equivalent PCT/US99/22690. A monoanionic bidentate ligand and two monoanionic ligands stabilize those catalyst precursors; they are activable with this invention's ionic cocatalysts. Other suitable Group-4-5 non-metallocene catalysts are bimetallocyclic catalyst compounds comprising two independently selected Group-4-5 metal atoms directly linked through two bridging groups to form cyclic compounds.

Invention catalyst systems can use other transition metal catalyst precursors that have a 2+ oxidation state as the additional olefin polymerization catalyst. Typical $Ni^{2+}$ and $Pd^{2+}$ complexes are diimines, see "New Pd(II)- and Ni(II)-Based Catalysts for Polymerization of Ethylene and α-Olefins", M. Brookhart, et al, *J. Am. Chem. Soc.,* 1995, 117, 6414-6415, WO 96/23010 and WO 97/02298. See additionally the related bis(imino) Group-8 and -9 organometallic compounds described by V. C. Gibson and others in "Novel olefin polymerization catalysts based on iron and cobalt", *Chem. Commun.,* 849-850, 1998.

Process

In the invention oligomerization processes, the process temperature may be −100° C. to 300° C., −20° C. to 200° C., or 0° C. to 150° C. Some embodiments select ethylene oligomerization pressures (gauge) from 0 kPa-35 MPa or 500 kPa-15 MPa.

The preferred and primary feedstock for the oligomerization process is the α-olefin, ethylene. But other α-olefins, including but not limited to propylene and 1-butene, may also be used alone or combined with ethylene.

In an embodiment, the catalyst system is reacted with ethylene, propylene, 1-butene, or a mixture of any two or all three of ethylene, propylene, and 1-butene.

Invention oligomerization processes may be run in the presence of various liquids, particularly aprotic organic liquids. The homogeneous catalyst system, ethylene, α-olefins, and product are soluble in these liquids. A supported (heterogeneous) catalyst system may also be used, but will form a slurry rather than a solution. Suitable liquids for both homo- and heterogeneous catalyst systems, include alkanes, alkenes, cycloalkanes, selected halogenated hydrocarbons, aromatic hydrocarbons, and in some cases, hydrofluorocarbons. Useful solvents specifically include hexane, toluene, cyclohexane, and benzene.

In an embodiment, the catalyst's activity exceeds 8000 moles of ethylene per mole transition metal per hour.

Also, mixtures of α-olefins containing desirable numbers of carbon atoms may be obtained. Factor K from the Schulz-Flory theory (see for instance B. Elvers, et al., *Ed. Ullmann's Encyclopedia of Industrial Chemistry*, Vol. A13, VCH Verlagsgesellschaft mbH, Weinheim, 1989, p. 243-247 and 275-276) serves as a measure of these α-olefins' molecular weights. From this theory, $$K = n(C_{n+2} \text{olefin})/n(C_n \text{olefin})$$

where $n(C_n$ olefin) is the number of moles of olefin containing n carbon atoms, and $n(C_{n+2}$ olefin) is the number of moles of olefin containing n+2 carbon atoms, or in other words the next higher oligomer of $C_n$ olefin. From this can be determined the weight (mass) fractions of the various olefins in the resulting product. The ability to vary this factor provides the ability to choose the then-desired olefins.

In an embodiment, the polymerization methods further comprising recovering a product comprising greater than 50 mol % of linear $C_4$-$C_{14}$ alpha-olefins based on the total weight of polymerized product. Alternately the product comprises greater than 80 mol % of linear $C_4$-$C_{14}$ alpha-olefins.

In another embodiment, the polymerization product comprises greater than 50 mol % of linear $C_4$ and $C_6$ alpha-olefins, alternately greater than 80 mol % of linear $C_4$ and $C_6$ alpha-olefins.

Invention-made α-olefins may be further polymerized with other olefins to form polyolefins, especially linear low-density polyethylenes, which are copolymers containing ethylene. They may also be homopolymerized. These polymers may be made by a number of known methods, such as Ziegler-Natta-type polymerization, metallocene catalyzed polymerization, and other methods, see for instance WO 96/23010, see for instance *Angew. Chem., Int. Ed. Engl.*, vol. 34, p. 1143-1170 (1995); European Patent Application, 416,815; and U.S. Pat. No. 5,198,401 for information about metallocene-type catalysts, and J. Boor Jr., *Ziegler-Natta Catalysts and Polymerizations*, Academic Press, New York, 1979 and G. Allen, et al., Ed., *Comprehensive Polymer Science*, Vol. 4, Pergamon Press, Oxford, 1989, pp. 1-108, 409-412 and 533-584, for information about Ziegler-Natta-type catalysts, and H. Mark, et al., Ed., *Encyclopedia of Polymer Science and Engineering*, Vol. 6, John Wiley & Sons, New York, 1992, p. 383-522, for information about polyethylene.

Invention-made α-olefins may be converted to alcohols by known processes, these alcohols being useful for a variety of applications such as intermediates for detergents or plasticizers. The α-olefins may be converted to alcohols by a variety of processes, such as the oxo process followed by hydrogenation, or by a modified, single-step oxo process (the modified Shell process), see for instance B. Elvers, et al., Ed., *Ullmann's Encyclopedia of Chemical Technology,* 5th Ed., Vol. A18, VCH Verlagsgesellschaft mbH, Weinheim, 1991, p. 321-327.

A set of exemplary catalyst precursors is set out below. These are by way of example only and are not intended to list every catalyst precursor that is within the scope of the invention.

Several structures are shown along with their corresponding name.

EXAMPLES

The following examples are presented to illustrate the discussion above. Although the examples may be directed toward certain embodiments of the present invention, they do not limit the invention in any specific way. In these examples, certain abbreviations are used to facilitate the description. These include standard chemical abbreviations for the elements and certain, commonly accepted abbreviations, such as: Me=methyl, Ph=phenyl, Cy=cyclohexyl, MAO=methylalumoxane, COD=cyclooctadiene and DME=ethylene glycol dimethyl ether.

All preparations were performed under an inert nitrogen atmosphere using standard Schlenk or glovebox techniques, unless mentioned otherwise. Dry solvents (toluene, diethyl ether, pentane, methylene chloride) were purchased as anhydrous solvents and further purified by passing them down an alumina (Fluka) column. Ethylene (99.9% ) was purchased from BOC (Surrey, United Kingdom). 2-(N,N-dimethlamino)-2'-(dicyclohexylphosphino)biphenyl and 2-(N,N-dimethlamino)-2'-(diphenylphosphino)biphenyl were purchased from Strem Chemicals, Inc. Tetramethyltin, nickel(II) bromide ethylene glycol dimethylether complex, and dichloro(1,5-cyclooctadiene)palladium(II) were purchased from Aldrich Chemical Company. Deuterated solvents were dried with CaH and vacuum distilled prior to use.

Some compounds prepared are illustrated below:

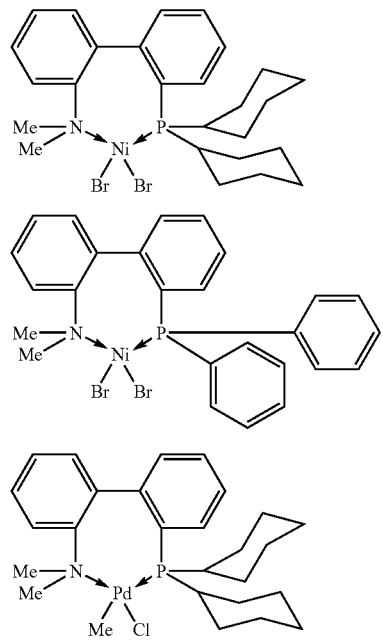

Compound 1

Compound 2

Compound 3

Preparation of 2-(N,N-dimethlamino)-2'-(dicyclo-hexylphosphino)biphenyl nickel dibromide (Compound 1).

$CH_2Cl_2$ (25 ml) was added to a Schlenk flask containing 2-(N,N-dimethlamino)-2'-(dicyclohexylphosphino)biphenyl (2.00 g, 5.10 mmol) and (DME)$NiBr_2$ (1.23 g, 4.0 mmol) in a dry box. A dark blue solution formed immediately upon mixing. This solution was stirred for 20 hours. Then, it was filtered and recrystallized from $CH_2Cl_2$/pentane. The product was washed three times with an additional 15 ml of pentane and dried for 1 hour under vacuum. A blue powder was isolated in 49.0% yield. The product was soluble in $CH_2Cl_2$. $^1$H NMR indicates that it is paramagnetic. Anal. Calcd for ($C_{26}H_{36}NPBr_2Ni$): C, 51.02%; H, 5.94%; N, 2.29%; P, 5.06%. Found: C, 50.72%; H, 6.10%; N, 2.12%; P, 5.02%. The IR (cm$^{-1}$, KBr): 272, v(Ni—Br). This compound has also been characterized by x-ray crystallography.

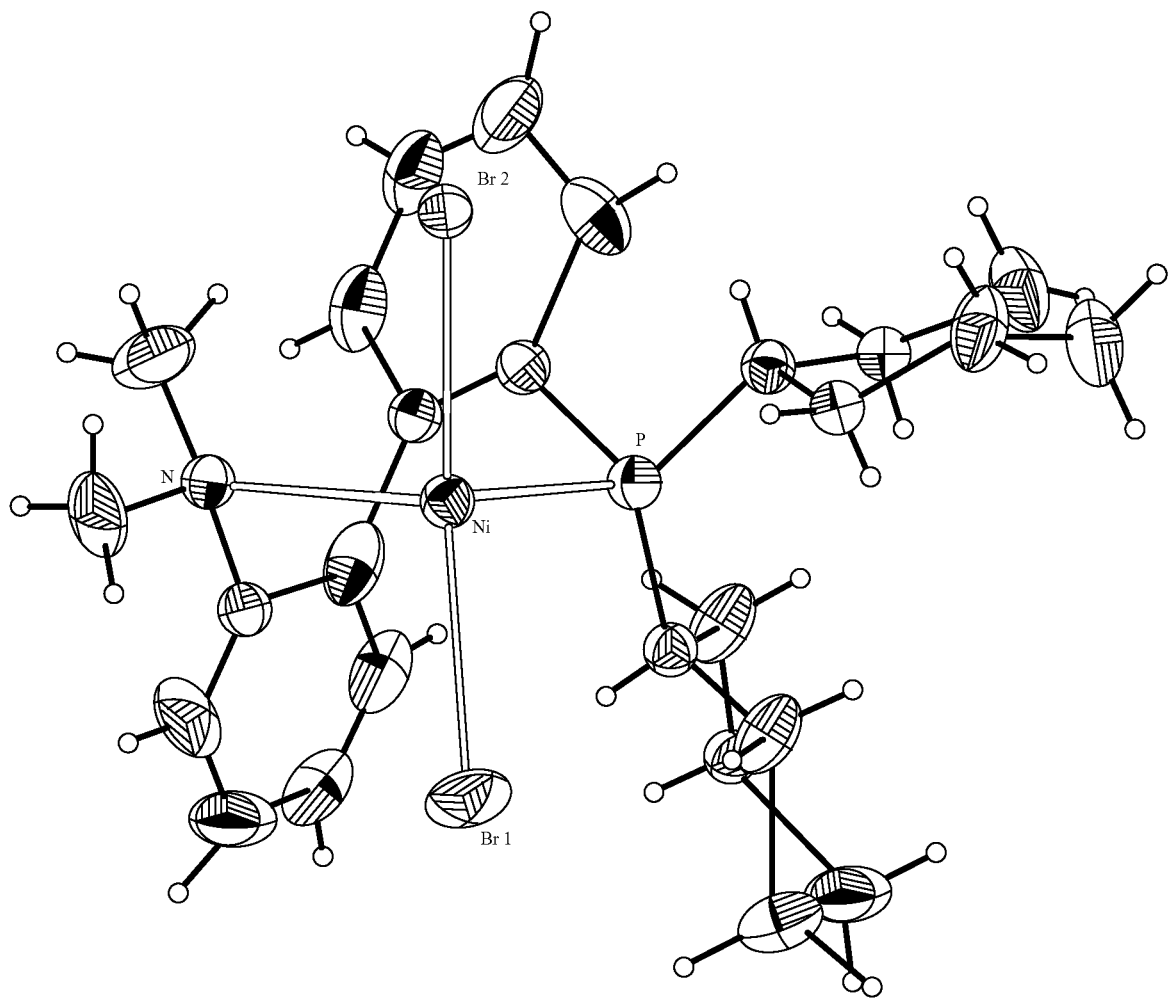

Preparation of 2-(N,N-dimethlamino)-2'-(diphenylphosphino)biphenyl nickel dibromide (Compound 2)

$CH_2Cl_2$ (25 ml) was added to a Schlenk flask containing the 2-(N,N-dimethlamino)-2'-(diphenylphosphino)biphenyl (2.00 g, 5.2 mmol) and (DME)NiBr$_2$ (1.30 g, 4.2 mmol) in a dry box. A green solution formed immediately upon mixing. This solution was stirred for 20 hours. Then, it was filtered and recrystallized from $CH_2Cl_2$/pentane. The product was washed three times with an additional 15 ml of pentane and dried for 1 hour under vacuum. A green powder was isolated in 69.3% yield. The product was soluble in $CH_2Cl_2$. $^1H$ NMR indicates that it is paramagnetic. Anal. Calcd for ($C_{26}H_{24}NPBr_2Ni$): C, 52.03%; H, 4.08%; N, 2.33%; P, 5.16%. Found: C, 1.20%; H, 4.24%; N, 2.14%; P, 5.29%.

Preparation of 2-(N,N-dimethylamino)-2'-(dicyclohexylphosphino)biphenyl palladium methyl chloride (Compound 3)

(COD)PdCl$_2$ (2.0 g, 7.0 mmol) was mixed with tetramethyltin (1.16 ml, 8.4 mmol) in $CH_2Cl_2$ (50 ml) at room temperature. The mixture was stirred overnight until the bright yellow color of the precursor had vanished. The resulting mixture was filtered through Celite yielding a pale yellow solution. The solvent was removed from that solution, leaving behind an off-white solid, (COD)PdClMe, which was washed twice with diethyl ether and dried under vacuum. A solution of the white (COD)PdClMe complex (0.775 g, 0.0029 mol dissolved in $CH_2Cl_2$) was reacted with 2-(N,N-dimethlamino)-2'-(dicyclohexylphosphino)biphenyl (1.78 g, 0.0045 mol). As a result, a light yellow palladium complex formed. $^1H$ NMR (250 MHz, $CD_2Cl_2$, δ, ppm): 0.88-2.94 m (22H, $2\times C_6H_{11}$); 1.06 d (3H, PdCH$_3$, $J_{PH}$=2.5 Hz); 2.87 s (6H, $2\times CH_3$); 6.75-7.68 m (8H, $2\times C_6H_4$). Anal. Calcd for ($C_{27}H_{39}NPClPd$): C, 58.91%; H, 7.16%; N, 2.55%; P, 5.63%. Found: C, 59.21%; H, 7.31%; N, 2.38%; P, 5.41%.

Oligomerization Reactions

Oligomerization reactions were run in 300 mL HastelloyC Parr reactor equipped with a mechanical stirrer. Catalyst (dissolved in 75 ml toluene) was added to the reactor under argon. Ethylene was added to the reactor at 100 psig, and then, the reactor was vented to maintain an atmosphere of ethylene. Methylalumoxane solution (Albemarle, 30 wt % in toluene) was then cannulated in to the reactor. This process caused catalyst activation to be completed in the presence of the monomer. After activation, the ethylene pressure was adjusted to the desired value. It was attempted to maintain the reactor temperature at room temperature; but in cases where the exotherm was very large, higher reaction temperatures were reached. After the reaction had run for an hour, the reactor was cooled in an acetone/dry ice bath and vented. The reaction was quenched with methanol. A sample of the product solution was analyzed by GC/MS after adding nonane as an internal standard. In the case of supported transition metal compounds, silica-loaded samples were prepared by adding a solution of the transition metal complex in methylene chloride to silica followed by overnight drying of the silica under vacuum. MAO was added to the reactor solution prior to adding the supported transition metal compound. The results of the oligomerization reactions are tabulated below in Table 2.

TABLE 2

Oligomerization Examples

| Catalyst[a] | $C_2$ (psig) | Final Rxn Temperature (° C.) | Activity (mol $C_2$/mol Ni · hr) | Product |
|---|---|---|---|---|
| 1 | 820 | 40 | 226,200 | Linear $C_4$ to $C_{14}$ (K* = 0.60)[b] |
| 1 | 100 | 30 | 26,700 | Primarily $C_4$ and $C_6$ (linear) |
| 1 | 800 | 25 | 155,000 | Primarily $C_4$ and $C_6$ (linear)[c] |
| 2 | 800 | 30 | 130,000 | $C_4$ |
| 2 | 100 | 30 | 8095 | $C_4$ |

[a]0.0075 mmol of catalyst
[b]*K is based on $C_{14}/C_{12}$ molar ratio for all isomers.
[c]After removing all volatiles at room temperature under vacuum, traces of higher oligomers were observed by NMR in the residue with 84 mol % of terminal olefins; GC/MS of the same residue showed $C_{16}$ to $C_{24}$ oligomers.

While certain representative embodiments and details have been shown to illustrate the invention, it will be apparent to skilled artisans that various process and product changes from those currently disclosed may be made without departing from this invention's scope. The appended claims define the invention's scope.

All cited patents, test procedures, priority documents, and other cited documents are fully incorporated by reference to the extent that this material is consistent with this specification and for all jurisdictions in which such incorporation is permitted.

Certain features of the present invention are described in terms of a set of numerical upper limits and a set of numerical lower limits. This specification discloses all ranges formed by any combination of these limits. All combinations of these limits are within the scope of the invention unless otherwise indicated.

The invention claimed is:

1. An olefin polymerization or oligomerization catalyst system comprising the reaction product of:
   (a) an activator selected from the group consisting of alumoxane, aluminum alkyl, alkyl aluminum halide, alkylaluminum alkoxide, boron compounds, hexafluoro phosphorus compounds, hexafluoro antimony compounds, and hexafluoro arsenic compounds; and
   (b) a catalyst precursor having the following formula:

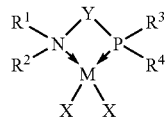

wherein:
(i) M is Ni, Fe, Co, Pd, or Pt;
(ii) N is nitrogen and is bonded to M;
(iii) P is phosphorus and is bonded to M;
(iv) R$^1$ and R$^2$ are independently selected from the group consisting of methyl, ethyl, propyl, butyl, pentyl, hexyl, heptyl, octyl, nonyl, decyl, undecyl dodecyl, cyclobutyl, cyclohexyl, phenyl, benzyl, phenethyl, tolyl, cyclopentyl, cycloheptyl, cyclooctyl, cyclononyl, cyclodecyl, and cyclododecyl;

(v) $R^3$ and $R^4$ are independently selected from the group consisting of methyl, ethyl, propyl, butyl, pentyl, hexyl, heptyl, octyl, nonyl, decyl, undecyl dodecyl, cyclobutyl, cyclohexyl, phenyl, benzyl, phenethyl, tolyl, cyclopentyl, cycloheptyl, cyclooctyl, cyclononyl, cyclodecyl, cyclododecyl and substituents represented by the formulas:

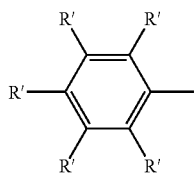 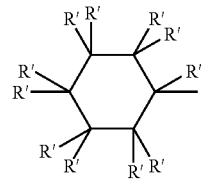

where R' are independently, hydrogen or $C_1$-$C_{50}$ hydrocarbyl radicals, and any two adjacent R' may independently be joined to form a saturated or unsaturated cyclic structure;

(vi) Y is butenyl or has one of the following formulas:

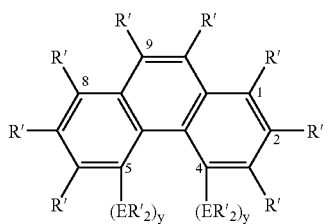

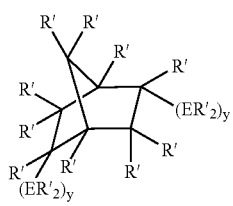

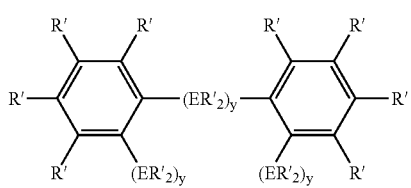

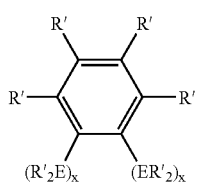 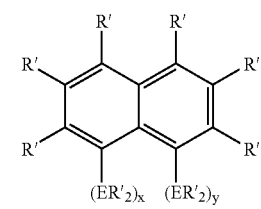

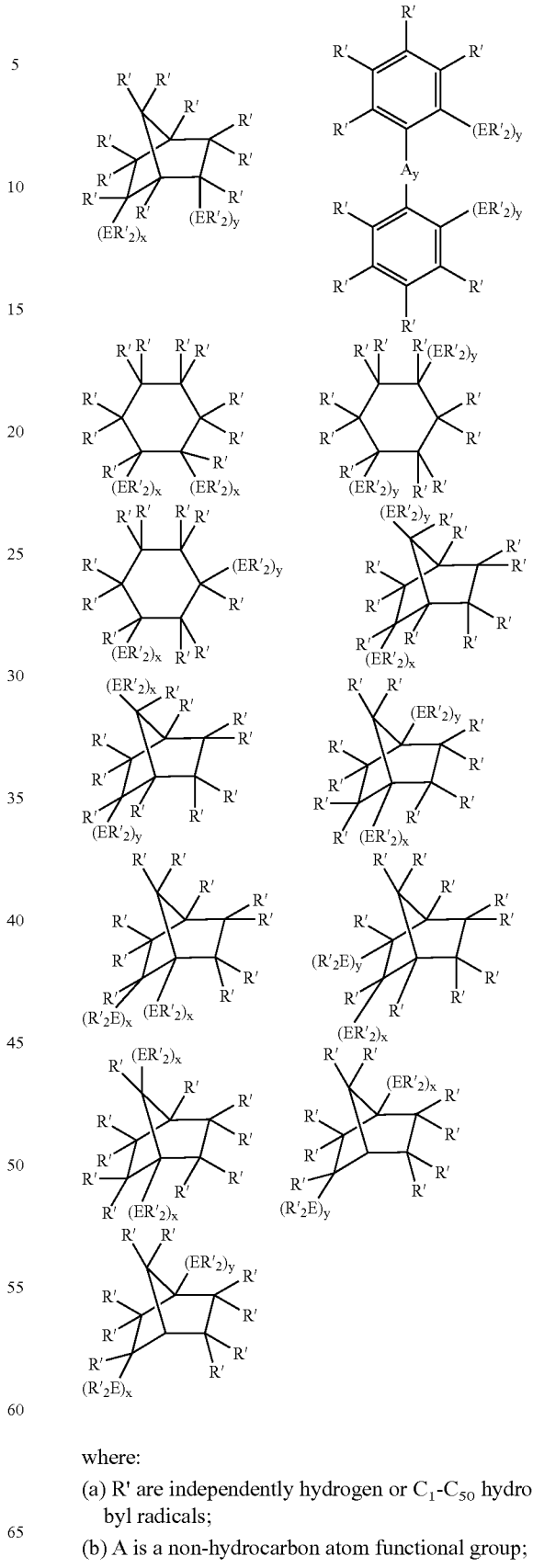

where:
(a) R' are independently hydrogen or $C_1$-$C_{50}$ hydrocarbyl radicals;
(b) A is a non-hydrocarbon atom functional group;
(c) E is a Group-14 element;

(d) x is an integer from 1 to 4; and
(e) y is an integer from 0 to 4; and
(vii) X are independently selected from the group consisting of chloride, bromide, iodide, methyl, ethyl, propyl, butyl, pentyl, hexyl, heptyl, octyl, nonyl, decyl, undecyl, dodecyl, methoxide, ethoxide, dimethylamide, diethylethoxide, and phenoxide,
wherein the olefin polymerization or oligomerization catalyst system exhibits an activity that exceeds 8000 moles of ethylene per mole of M per hour.

2. The catalyst system of claim 1, wherein $R^3$ and $R^4$ are selected from the group consisting of cyclohexyl, phenyl, benzyl, phenethyl, and tolyl.

3. The catalyst system of claim 1, wherein $R^1$, $R^2$, $R^3$, and $R^4$ are independently selected from the group consisting of methyl, ethyl, propyl, butyl, cyclohexyl, phenyl, tolyl, benzyl, and phenethyl.

4. The catalyst system of claim 1, wherein A is selected from the group consisting of C=O, C=S, O, S, $SO_2$, NR*, PR*, BR*, $SiR*_2$, and $GeR*_2$, where R* is independently a hydrocarbyl or halocarbyl radical.

5. The catalyst system of claim 1, wherein Y is biphenyl.

6. The catalyst system of claim 1, wherein X are independently chloride, bromide, iodide, methoxide, ethoxide, dimethylamide, diethylethoxide, or phenoxide.

7. The catalyst system of claim 1, wherein the activator comprises $B(C_6F_5)_3$ or $B(C_6H_5)_3$.

8. The catalyst system of claim 1, wherein the activator comprises a cyclic oligomeric aluminum compound represented by the formula $(R''-Al-O)_n$, or a linear oligomeric aluminum compound represented by the formula $R''(R''-Al-O)_nAlR''_2$, wherein R" is independently a $C_1$-$C_{20}$ alkyl radical, and wherein n is an integer from 1-50.

9. The catalyst system of claim 1, wherein the activator is methylalumoxane.

10. The catalyst system of claim 1, wherein the activator is triethylaluminum, diethylaluminum chloride, triisobutylaluminum, tri-n-octylaluminum, or a combination thereof.

11. The catalyst system of claim 1, wherein the activator is $[Me_2PhNH][B(C_6F_5)_4]$, $[Bu_3NH][BE_4]$, $[NH_4][PF_6]$, $[NH_4][SbF_6]$, $[NH_4][AsF_6]$, $[NH_4][B(C_6H_5)_4]$, $B(C_6F_5)_3$, $B(C_6H_5)_3$, or a combination thereof.

12. The catalyst system of claim 1, wherein the catalyst is deposited on a solid support, the solid support comprising polymeric materials or refractory oxide materials.

13. A catalyst system comprising the reaction product of:
(a) the catalyst system of claim 1 and
(b) olefin monomer(s) comprising ethylene, propylene, 1-butene, or a mixture of any two or all three of ethylene, propylene, and 1-butene.

14. The catalyst system of claim 1, further comprising at least one additional olefin polymerization catalyst.

15. An oligomerization or polymerization method comprising contacting at least one catalyst system of claim 1 with alpha-olefin comprising ethylene, wherein the catalyst's activity exceeds 8000 moles of ethylene per mole of M per hour.

16. The method of claim 15, further comprising recovering a product comprising greater than 50 mol % of linear $C_4$-$C_{14}$ alpha-olefins based on the total weight of polymerized product.

17. The method of claim 15, wherein the product comprises greater than 80 mol % of linear $C_4$-$C_{14}$ alpha-olefins.

18. The method of claim 15, wherein the product comprises greater than 50 mol % of linear $C_4$ and $C_6$ alpha-olefins.

19. The method of claim 15, wherein the product comprises greater than 80 mol % of linear $C_4$ and $C_6$ alpha-olefins.

20. The method of claim 15, comprising reacting
(a) the catalyst system and
(b) olefin monomer(s) comprising ethylene, propylene, 1-butene, or a mixture of any two or all three of ethylene, propylene, and 1-butene.

21. The method of claim 15, wherein the oligomerization or polymerization is run in the presence of an aprotic organic liquid.

22. The catalyst system of claim 1, further comprising an aprotic organic liquid.

23. The catalyst system of claim 13, wherein the olefin monomer(s) consists essentially of ethylene, propylene, 1-butene, and mixtures thereof.

24. The method of claim 20, wherein the catalyst system is reacted with olefin monomer(s) consisting essentially of ethylene, propylene, 1-butene, and mixtures thereof.

25. The catalyst system of claim 1, wherein the catalyst precursor has the formula:

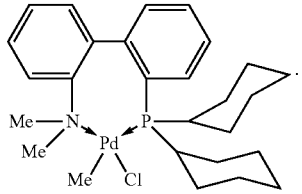

Formula XXIII

* * * * *